United States Patent [19]

Rauchwerger

[11] Patent Number: 4,663,614
[45] Date of Patent: May 5, 1987

[54] HYDROCARBON DETECTOR SYSTEM

[76] Inventor: George P. Rauchwerger, 147 Cromart Ct., Sunnyvale, Calif. 94087

[21] Appl. No.: 762,629

[22] Filed: Aug. 5, 1985

[51] Int. Cl.⁴ .............................................. G08B 21/00
[52] U.S. Cl. .................................... 340/605; 210/315; 210/924; 324/65 P; 340/620
[58] Field of Search ............... 340/605, 602, 604, 620; 324/65 P; 210/85 R, 86, 96.1, 924, 315; 73/304 R

[56] References Cited

U.S. PATENT DOCUMENTS 4,563,674 1/1986 Kobayashi ........................ 340/620

Primary Examiner—James L. Rowland
Assistant Examiner—Daniel Myer
Attorney, Agent, or Firm—Julian Caplan

[57] ABSTRACT

A probe comprising an electrically conductive polymer and a pair of electrodes is placed to be contacted by the chemical. Contact changes the molecular structure or arrangement and changes the resistivity of the polymer, which is measured to actuate an indicator and/or alarm. The probe may be incorporated in a float. The chemical detector may be combined with a water detector.

11 Claims, 10 Drawing Figures

HYDROCARBON DETECTOR SYSTEM

BACKGROUND OF THE INVENTION

1. Field of the Invention

This invention relates to a system for detecting the presence of chemicals whether they be in liquid, vapor or gaseous state. More particularly the system detects hazardous chemicals such as gasoline, trichloroethylene, alcohol, and other solvents and hydrocarbons. The system is particulary useful in detecting leakage of such chemicals, as well as others, from tanks into surrounding areas where they may contaminate drinking water and the like. The term "chemicals" is used broadly in this patent to indicate the foregoing and similar chemicals.

When the system detects the presence of chemicals, an alarm which may be either audible or visual is turned on.

The system employs a probe to detect the chemical in a double walled tank or in a monitoring well drilled for this purpose next to an underground tank, when floating on the water and in other environments. Detection by the probe energizes the alarm system.

Other objects of the invention are that it is safe in the sense that it does not cause fires or explosions and is relatively inexpensive. The probe has no moving parts and requires only a single length of wire rather than a collapsible length which is required in other floating probes.

2. Description of Related Art

Kashikawa U.S. Pat. No. 3,970,863 discloses a petroleum leakage detection system comprising an S-B-S block copolymer which is made electro-conductive by coating or filling it with a conductive metal powder, foil or the like. When a petroleum product comes in contact with the copolymer, the latter swells, thereby separating the dispersed metal and causing a decrease in conductivity. The disclosure of Kashikawa is the use of an S-B-S block copolymer which swells. The present invention operates by a change in conductivity of the copolymer as a result of changes in the conductivity of the materials rather than the spatial separation thereof.

Luden U.S. Pat. No. 3,579,097 discloses an ammonia gas detecting system comprising a non-porous, non-conductive probe coated with a liquid film. When ammonia is absorbed by the film, the conductivity is changed and is detected. Thus this reference works only for gases which are readily absorbable into a liquid film and then affect the conductivity thereof. Luden does not disclose a polymer material such that its conductivity is increased when gas is absorbed. In the present invention the conductivity of the copolymer is decreased.

Hsu U.S. Pat. No. 3,562,731 discloses a water detecting system which includes an alarm but is otherwise different from the present invention.

Hedeby U.S. Pat. No. 1,786,843 shows a time clock for a pipe leak detector system which is activated once the leak is detected.

Other patents showing detecting hazardous gases or liquids wherein the conductivity of an element is monitored include U.S. Pat. Nos. 2,716,721; 2,760,152; 3,262,106; 3,720,797; 3,966,580; 3,992,267 and 4,145,913.

SUMMARY OF THE INVENTION

A probe consisting of an electrically conductive polymer such as foam, film or similar material is impregnated with a carbon solution. Imbedded in spaced relationship in the polymer are two electrodes. Contact with a chemical causes a change in molecular structure or arrangement of the polymer, affecting its resistivity. Change in resistivity is measured and at a certain level the alarm is actuated.

The conductive medium may be a carbon solution which can be applied to many materials including plastics and films. Conductive foam and related carbon impregnated materials are presently on the market as antistatic media for CMOS chips.

The hazardous chemicals detected by this system include hydrocarbons, gasoline, chlorinated hydrocarbon such as TCE and PCE.

The chemical probe hereinafter described in detail may be combined in one unit with a water detection probe. The latter employs two metal electrodes which, when they come in contact with water, conduct and cause an alarm to be energized.

The probe may be incorporated in a float or into a piece of extruded plastic similar to "DIP tubes" used in the electronics industry.

The probe may also detect vapor and gas without the presence of liquid. The vapor or gas comes in contact with a low density foam causing an increase in resistivity.

The circuit which is used in the present invention uses extremely low current and may be battery operated if desired. An LCD clock may be incorporated in the circuit to indicate how long the leak has been detected. Other details of the electrical system are set forth below.

Other objects of the present invention will become apparent upon reading the following specification and referring to the accompanying drawings in which similar characters of reference represent corresponding parts in each of the several views.

IN THE DRAWINGS

DESCRIPTION OF PREFERRED EMBODIMENTS

Figure 4:
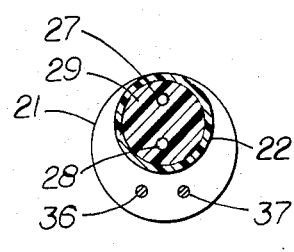
FIG. 4 is a sectional view taken substantially along the line 4—4 of FIG. 3.
Figure 3:
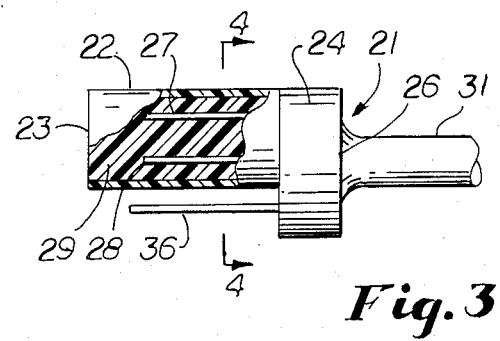
FIG. 3 is a side elevational view of the probe of FIG. 1 partially broken away in section to reveal internal construction.

Directing attention first to the form of the invention shown in FIGS. 1-4, probe 21 has a plastic casing 22 formed with an open end 23 through which liquid may enter and a closed end 24 which is sealed by seal 26. Within casing 22 are space metal electrodes 27, 28 which may be plated with gold to prevent corrosion and to ensure a reliable contact. These electrodes 27, 28 are embedded in intimate contact with a conductive medium such as high density foam 29. The foam 29 is an electrically conductive polymer impregnated with a carbon solution characterized by the fact that its molecular structure or arrangement changes and its resistivity is affected very rapidly when a chemical to be detected comes in contact therewith.

Figure 1:
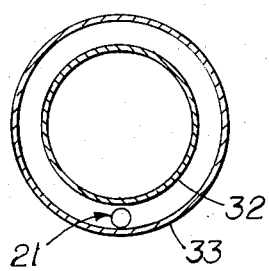
FIG. 1 is an end elevational view of a probe in accordance with the present invention.
Figure 2:
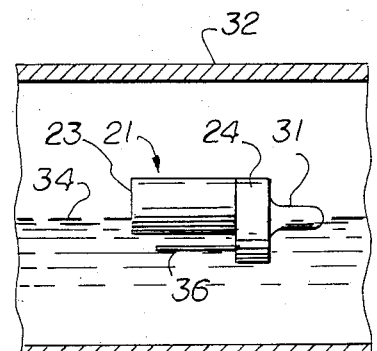
FIG. 2 is a schematic view showing in reduced scale a probe in accordance with FIG. 1 floating on a liquid.

The foregoing described probe may be employed in various environments. As shown in FIGS. 1 and 2, the probe 21 may be installed between the inner wall 32 and outer wall 33 of a double walled tank such as used for gasoline storage. It floats on the surface of the liquid 34 which may have leaked from the inner tank into the space between the walls. It will be understood that the probe may be placed in many other environments.

The foregoing described structure is sufficient where no water is to be detected. However, where desired, the probe 21 may be made as a water detector by adding two spaced apart electrodes 36, 37, preferably gold plated, supported by closed end 24 and connected to additional wires in cable 31. The disposition of weight in the probe 21 is such that the electrodes 36 and 37 float downmost and are at the bottom for continuous water detection. When water comes in contact with electrodes 36, 37, a low resistance is detected at the alarm circuit and an alarm is sounded. When chemical liquid enters the open end 23, it is absorbed by the foam 29 causing the carbon molecules in the foam to combine with the molecules from the hydrocarbon liquid or other chemical, changing the resistance of the foam. This resistance generally increases until it reaches an infinite resistivity and thus the conductivity in turn becomes zero, whereupon an alarm, a clock and identification lights are energized, as hereinafter explained in the description of the circuitry.

Figure 5:
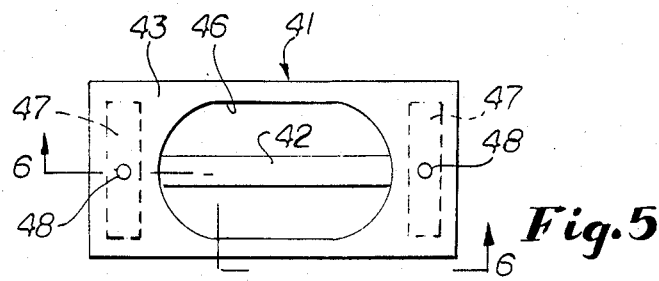
FIG. 5 is a side elevational view of a vapor detecting probe.
Figure 6:
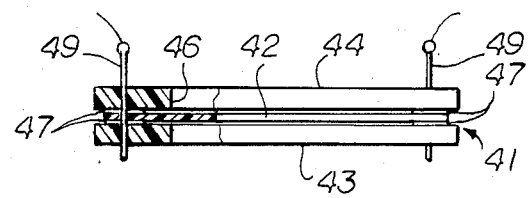
FIG. 6 is a plan view thereof.

Directing attention to FIGS. 5 and 6, a vapor and gas detection probe 41 is disclosed. This probe uses the same materials as that of FIGS. 1-4 but is made much more sensitive by locating a very thin piece of conductive foam 42 between two contacts 47 on a printed circuit board 43 or 44 with a window 46 formed in each of the boards 43, 44 for air circulation. The boards 43, 44 are used to sandwich the foam 42 so that reliable contacts are made. Representative approximate dimensions may be 1" L, 0.25" W, and 0.12" T.

Vapor or gas coming in contact with foam 42 increases its resistivity rapidly and energizes an electric circuit as hereinafter described.

The traces 47 of each of the boards 43, 44 making up the probe act as pressure contacts with the thin foam 42. To ensure reliability and ease of manufacture, the boards 43 and 44 are preferably made identical and the connecting holes 48 are plated through. Wires 49 are soldered on both sides.

Figure 8:
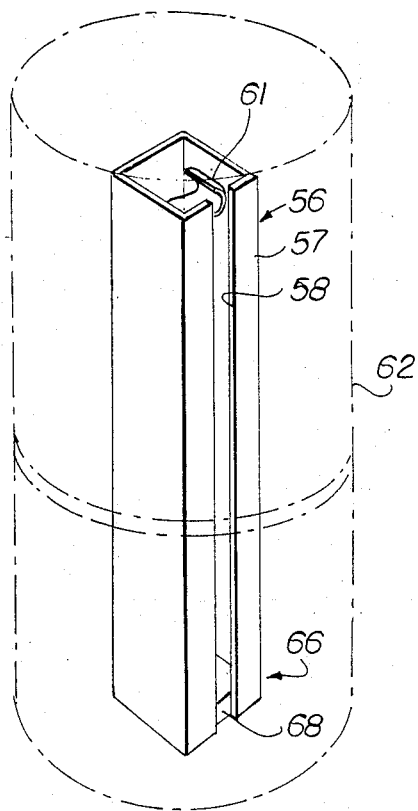
FIG. 8 is a schematic perspective view showing the probe of FIG. 7 in a conduit or monitoring well.
Figure 7:
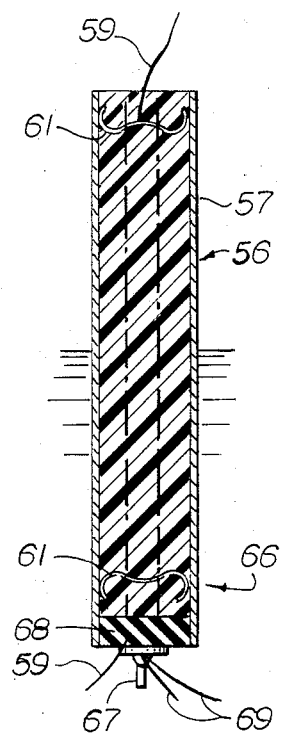
FIG. 7 is a vertical mid-section of a conductive plastic tube modification of the invention shown partially immersed in a liquid.

Directing attention to FIGS. 7 and 8, a solid state floatless probe is disclosed which replaces any float mechanism which may previously have been used to detect the same liquids utilizing other principles.

Probe 56 is preferably a single piece of extruded plastic with conductive carbon compound molded within it. Such products are used in anti-static "DIP" tubes for the electronics industry. The length and shape of the probe tube 57 may be varied. The probe 57 may be located within a well 62 or any body of water where it is desirable to detect a chemical spill of such chemicals as hydrocarbons, which float on water. It is not necessary that water be present as it is the chemical which changes the probe characteristics. When these chemicals come in contact with the probe, the resistivity and thus the conductivity of the material changes rapidly. The change is measured by the electronic circuit as in the previous modification. The probe 56 detects the chemical presence at any point throughout its length. Preferably the probe does not float but is stationary.

Floating varieties of chemical detectors have many problems and are expensive. The present invention has no moving parts, it requires only a single length of wire as distinguished from the collapsible length which moves with a floating type probe in which instances the float has to be designed to support the weight of the wire. The probe 56 of the present invention detects minute spills or very thin films of chemicals floating on the water as in contrast with mechanical types of detectors of the floating variety which require about ⅛ inch or more of the chemical on the water.

The chemical, when in contact with the tube 57 combines with the carbon impregnated therein, in essence leaching out the carbon molecules from the contact area, leaving a high resistance ring (infinite resistance or zero conductivity with time). As the ring will occur at the water level at the time of the leak, one can measure the water table level by measuring the distance from the probe bottom to the ring.

Probe 56 may operate in a dry well rather than one filled with liquid. Of course in such situation the probe does not float but is suspended in the well.

Directing attention to FIG. 8, the tube 67 may be square or other shape having a longitudinally extending opening 58. Lead wires 59 at top and bottom are electrically connected to spring clips 61 which make pressure contact at both ends of the probe in the same manner as a common resistor. The tube 57 may be of any shape in lengths so long as it is rigid enough to remain upright in a well 62 or other confined area where chemicals may pollute another liquid. The polluting chemical enters through the opening 58, and leaches out the carbon in tube 57, affecting the resistance between the clips 61.

A water detector 66 may be incorporated at the bottom of probe 56 by adding an electrode 67 embedded in an insulator 68 and connected to wires 69. Two of the wires are common as in conventional combination probes. This allows the probe itself to act as one of the electrodes for water detection. The wires are preferably routed through the tube but are shown outside merely for clarity. Water detection is accomplished by a low resistance indication when the electrode 67 and the probe body 57 come in contact with the water. When the chemical liquid comes in contact with the conductive plastic, the resistance path is effectively broken or at least goes very high at the area where the chemical comes in contact with the probe. The rest of this operation is explained above.

Figure 9:
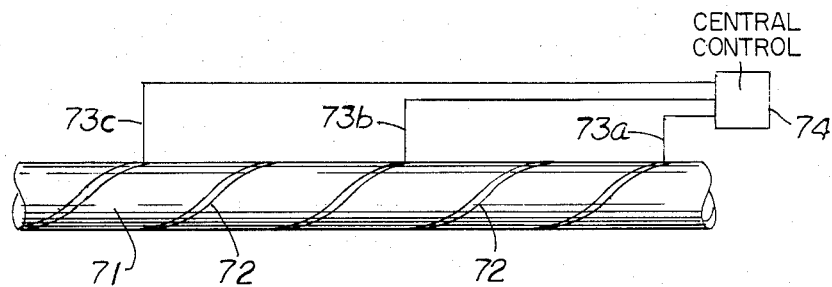
FIG. 9 is a schematic side elevational view of a modification employing conductive film tape.

Directing attention to FIG. 9, the invention is shown applied to a pipeline 71 to detect leaks of chemicals conveyed therein. Conductive film tape 72 is spirally wound around the pipe. At spaced intervals, wires 73a, 73b, 73c are connected to the tape. The remote ends of the wires are received in a central control 74. As a practical example, remote stations with telephone lines connecting the wires to the spaced intervals on the tape 72 may be used. Operation of the device is essentially the same as in the preceding modifications—i.e., if there is a leak in the pipe 71, the chemical causes a deterioration of the tape 72 at the point of leakage and this is measured as in the preceding modifications.

Figure 10:
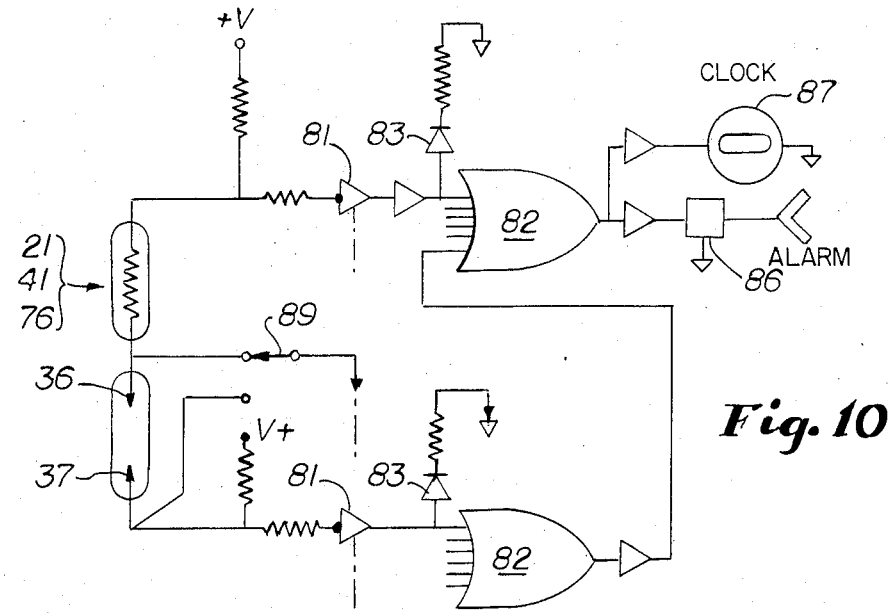
FIG. 10 is a schematic circuit diagram showing incorporation of both chemical and water probes into an alarm system.

FIG. 10 shows a schematic wiring diagram for a combination chemical detector and water detector. It will be understood that if the water detector is not incorporated in a probe such as probe 21, 41, 76, then the water detecting portion of the circuit is not used. The circuit is in essence a high resistance comparison circuit and when the probe resistance changes the change is detected by inverters 81 which turn "ON" thereby energizing gates 82 and LED indicators 83. The circuit will accommodate up to seven sets of probes with corresponding gates 82. The gates 82 send a signal to the audible alarm 86 and also start the clock 87 to indicate when the leak occurred. More gates may be cascaded to accept additional probes.

Where a water detector is incorporated with the probe or independently of the probe, its electrodes 36, 37, etc., are wired as shown in FIG. 10. The water indicator has its own inverter 81 and gate 82 and its own indicator 83. By wiring the gate 82 into one of the gates 82 for the chemical detector, the alarm 86 and clock 87 may be used for both purposes.

A test switch 89 remotely tests each of the probes by lighting the appropriate LED indicator 83, indicating to the operator whether the probes are functioning correctly. Switch 89 also tests the other electronics by turning on the clock 87 and alarm 86.

What is claimed is:

1. A probe for detecting the presence of a hazardous chemical comprising a vertically elongated body fixed in position in a space where such chemical may be present, said body being electrically conductive and formed of a polymer impregnated with carbon, said polymer being of a class including high density foam and rigid plastic characterized by the fact that a pre-selected class of chemicals coming in contact with said body remove at least some of said carbon and thereby increase the resistivity of said body, said class including hydrocarbon liquids and vapors, said body having first and second opposite ends, said ends being spaced apart;

a first electrode in electrical contact with said first end and a second electrode in electrical contact with said second end;

whereby a layer of said chemical acts upon said body substantially only in the area of said body at the level of said layer.

2. A probe according to claim 1 suitable to detect chemical vapors and gases wherein said body is formed in a very thin layer and which further comprises a board having a window for circulation of said vapors and gases, said body extending across said window, said first and second electrodes being mounted on said board in electrical contact with said ends.

3. A probe according to claim 1 which further comprises a pipe, said body being a tape spirally wound on said pipe, said electrodes contacting said tape at spaced intervals.

4. A probe according to claim 1 which further comprises a casing of chemically impervious material surrounding said body, said casing being formed with an open end for ingress of chemical.

5. An alarm system comprising a probe according to claim 1, a circuit comprising a source of current, said first and second electrodes, a detector sensing changes in resistance between said first and second electrodes, and indicator means indicating the amount of resistance sensed.

6. A system according to claim 5 in which said circuit further comprises an alarm and alarm actuating means responsive to increase in resistance above a pre-selected amount.

7. A system according to claim 6 in which said circuit further comprises a clock, said clock being energized by said alarm actuating means.

8. A system according to claim 5 in which said probe has at least a third electrode positioned so that water contacting said probe closes a second circuit between said second and third electrodes, said second circuit further comprising said third electrode and a water detector alarm sensing closing of said circuit between said second and third electrodes.

9. A system according to claim 8 in which said circuit further comprises a water alarm and a water alarm actuating means responsive to closing of said circuit between said second and third electrodes.

10. A system according to claim 9 in which said circuit futher comprises a clock, said clock being energized by said alarm actuating means.

11. A probe according to claim 1 which further detects the presence of water comprising a third electrode fixed spaced from said body spaced from said second electrode whereby water closes a circuit between said second and third electrodes.

* * * * *